(12) United States Patent
Wang et al.

(10) Patent No.: US 12,064,482 B2
(45) Date of Patent: Aug. 20, 2024

(54) TRIPLET-TRIPLET ENERGY TRANSFER WITH LIGHT EXCITATION AT LONG WAVELENGTHS AND METHODS THEREOF

(71) Applicant: THE UNIVERSITY OF HONG KONG, Hong Kong (CN)

(72) Inventors: Weiping Wang, Hong Kong (CN); Wen Lyu, Hong Kong (CN)

(73) Assignee: THE UNIVERSITY OF HONG KONG, Hong Kong (CN)

(*) Notice: Subject to any disclaimer, the term of this patent is extended or adjusted under 35 U.S.C. 154(b) by 640 days.

(21) Appl. No.: 17/262,452

(22) PCT Filed: Aug. 21, 2019

(86) PCT No.: PCT/CN2019/101689
§ 371 (c)(1),
(2) Date: Jan. 22, 2021

(87) PCT Pub. No.: WO2020/038382
PCT Pub. Date: Feb. 27, 2020

(65) Prior Publication Data
US 2021/0228719 A1    Jul. 29, 2021

Related U.S. Application Data

(60) Provisional application No. 62/720,436, filed on Aug. 21, 2018.

(51) Int. Cl.
*A61K 41/00* (2020.01)
*A61K 31/196* (2006.01)
(Continued)

(52) U.S. Cl.
CPC ........ *A61K 41/0042* (2013.01); *A61K 31/196* (2013.01); *A61K 47/545* (2017.08); *A61K 47/6907* (2017.08); *A61K 47/6921* (2017.08)

(58) Field of Classification Search
CPC ............. A61K 41/0042; A61K 31/196; A61K 47/545; A61K 47/6907; A61K 47/6921; A61K 47/62
See application file for complete search history.

(56) References Cited

FOREIGN PATENT DOCUMENTS

| CN | 104718273 A | 6/2015 |
|---|---|---|
| CN | 104761578 A | 7/2015 |
| WO | 2017004310 A1 | 1/2017 |

OTHER PUBLICATIONS

Askes, et al. "Red Light-Triggered CO Release from Mn 2 (CO) 10 Using Triplet Sensitization in Polymer Nonwoven Fabrics." Journal of the American Chemical Society, vol. 139, No. 43, Nov. 2017, pp. 15292-19295. https://doi.org/10.1021/jacs.7b07427. (Year: 2017).*

(Continued)

*Primary Examiner* — Clinton A Brooks
*Assistant Examiner* — Kyle Nottingham
(74) *Attorney, Agent, or Firm* — Leason Ellis LLP

(57) ABSTRACT

The field of various phototriggered drug release and photoreactions, including reactions generally based on triplet-triplet energy transfer with light excitation at long wavelengths. Systems and methods for absorbing energy in a photosensitizer, and methods for making or using such systems, kits including such systems. The systems and methods comprise transferring that energy by triplet-triplet energy transfer to cleave a cleavable or other active moiety, for instance, in order to cause the release of a releasable moiety. In some cases, these may be contained within a suitable carrier material, for example, a particle or a micelle. Such systems and methods may be used in a variety of applications, including various biological or physical applications. For example, such systems and methods may be useful for delivering drugs or other releasable moieties to regions of a subject.

16 Claims, 15 Drawing Sheets

(51) Int. Cl.
   *A61K 47/54*   (2017.01)
   *A61K 47/69*   (2017.01)

(56) References Cited

OTHER PUBLICATIONS

Singh-Rachford, Tanya N., and Felix N. Castellano. "Triplet Sensitized Red-to-Blue Photon Upconversion." The Journal of Physical Chemistry Letters, vol. 1, No. 1, Jan. 2010, pp. 195-200. https://doi.org/10.1021/jz900170m. (Year: 2010).*
Huang, Ling, et al. "Expanding Anti-Stokes Shifting in Triplet-Triplet Annihilation Upconversion for In Vivo Anticancer Prodrug Activation." Angewandte Chemie International Edition, vol. 56, No. 46, Nov. 2017, pp. 14400-14404. Supplementary Information. (Year: 2017).*
Slanina, Tomáš, et al. "In Search of the Perfect Photocage: Structure-Reactivity Relationships in Meso-Methyl BODIPY Photoremovable Protecting Groups." Journal of the American Chemical Society, vol. 139, No. 42, Oct. 2017, pp. 15168-15175. Supplementary Information. (Year: 2017).*
Karimi, Mahdi, et al. "Smart micro/nanoparticles in stimulus-responsive drug/gene delivery systems." Chemical Society Reviews 45.5 (2016): 1457-1501.
Liu, Zhuang, et al. "Stimuli-responsive smart gating membranes." Chemical Society Reviews 45.3 (2016): 460-475.
Shen, Yong, et al. "Biodegradable stimuli-responsive polypeptide materials prepared by ring opening polymerization." Chemical Society Reviews 44.3 (2015): 612-622.
Karimi, Mahdi, et al. "Smart nanostructures for cargo delivery: uncaging and activating by light." Journal of the American Chemical Society 139.13 (2017): 4584-4610.
Solomek, Tomas, et al. "Searching for improved photoreleasing abilities of organic molecules." Accounts of chemical research 48.12 (2015): 3064-3072.
Rwei, Alina Y et al., "Photoresponsive nanoparticles for drug delivery." Nano today 10.4 (2015): 451-467.
Zhou, Jing, et al. "Upconversion luminescent materials: advances and applications." Chemical reviews 115.1 (2015): 395-465.
Wang, Feng et al., "Recent advances in the chemistry of lanthanide-doped upconversion nanocrystals." Chemical Society Reviews 38.4 (2009): 976-989.
Zhao, Jianzhang et al., "Triplet-triplet annihilation based upconversion: from triplet sensitizers and triplet acceptors to upconversion quantum yields." Rsc Advances 1.6 (2011): 937-950.
Liu, Jianan, et al. "NIR-triggered anticancer drug delivery by upconverting nanoparticles with integrated azobenzene-modified mesoporous silica." Angewandte Chemie 125.16 (2013): 4471-4475.
Zhao, Lingzhi, et al. "Near-infrared photoregulated drug release in living tumor tissue via yolk-shell upconversion nanocages." Advanced Functional Materials 24.3 (2014): 363-371.
Wang, Weiping, et al. "Efficient triplet-triplet annihilation-based upconversion for nanoparticle phototargeting." Nano letters 15.10 (2015): 6332-6338.
Liu, Qian, et al. "Enhanced precision of nanoparticle phototargeting in vivo at a safe irradiance." Nano letters 16.7 (2016): 4516-4520.
Huang, Ling, et al. "Expanding anti-Stokes shifting in triplet-triplet annihilation upconversion for in vivo anticancer prodrug activation." Angewandte Chemie 129.46 (2017): 14592-14596.
Goswami, Pratik P., et al. "BODIPY-derived photoremovable protecting groups unmasked with green light." Journal of the American Chemical Society 137.11 (2015): 3783-3786.
Slanina, Tomáš, et al. "In search of the perfect photocage: Structure-reactivity relationships in meso-methyl BODIPY photoremovable protecting groups." Journal of the American Chemical Society 139.42 (2017): 15168-15175.
Li, Ling-Ling, et al. "BODIPY-based two-photon fluorescent probe for real-time monitoring of lysosomal viscosity with fluorescence lifetime imaging microscopy." Analytical chemistry 90.9 (2018): 5873-5878.
Hoskere, Anila, et al. "Polysulfide-triggered fluorescent indicator suitable for super-resolution microscopy and application in imaging." Chemical Communications 54.30 (2018): 3735-3738.
Zhu, Hao, et al. "An "enhanced PET"-based fluorescent probe with ultrasensitivity for imaging basal and elesclomol-induced HClO in cancer cells." Journal of the American Chemical Society 136.37 (2014): 12820-12823.
Mendive-Tapia, Lorena, et al. "Preparation of a Trp-BODIPY fluorogenic amino acid to label peptides for enhanced live-cell fluorescence imaging." nature protocols 12.8 (2017): 1588.
Liu, Qian, et al. "A general strategy for biocompatible, high-effective upconversion nanocapsules based on triplet-triplet annihilation." Journal of the American Chemical Society 135.13 (2013): 5029-5037.
Lou, Zhangrong, et al. "Different quenching effect of intramolecular rotation on the singlet and triplet excited states of Bodipy." The Journal of Physical Chemistry C 122.1 (2018): 185-193.
International Search Report and Written Opinion in Corresponding International Patent Application No. PCT/CN2019/101689 mailed Nov. 26, 2019. 8 pages.
International Preliminary Report on Patentability in Corresponding PCT Application No. PCT/CN2019/101689 mailed Feb. 23, 2021. 4 pages.

* cited by examiner

TRIPLET-TRIPLET ENERGY TRANSFER WITH LIGHT EXCITATION AT LONG WAVELENGTHS AND METHODS THEREOF

CROSS-REFERENCE TO RELATED PATENT APPLICATIONS

This application is a U.S. National Stage Application under 35 U.S.C. § 371 of International Patent Application No. PCT/CN2019/101689, filed Aug. 21, 2019, which claims the benefit of priority of U.S. Patent Application No. 62/720,436 filed Aug. 21, 2018, both of which are incorporated by reference in their entireties. The International Application was published on Feb. 27, 2020, as International Publication No. WO 2020/038382 A1.

1. FIELD

The present disclosure generally relates to various phototriggered drug release and photoreactions, including reactions generally based on triplet-triplet energy transfer with light excitation.

2. BACKGROUND

Drug delivery plays an important role in cancer treatment. A site-specific and controllable drug release is highly desirable as it can reduce drug dosage to decrease side-effects and increase therapeutic effect. To address this issue, a variety of stimuli-responsive drug delivery systems have been developed.[1] The stimuli adopted in these drug delivery systems include light, pH, electric/magnetic field, ultrasound, thermo, specific biomolecules and so on. Compared to other stimuli, light irradiation could be easily manipulated with controllable power and exposure time. Moreover, the development of laser beam technique also provides an efficient solution for precise drug release in tumors, which makes photoresponsive drug delivery a promising strategy in cancer medicine at present.[2]

Photoresponsive systems commonly contain photoisomerizable groups (azobenzene, spiropyran and dithienylethene) or photocleavable groups (o-nitrobenzyl and coumarin-4-ylmethyl), whose chemical structures change under photoexcitation.[3] However, these photoresponsive groups usually require ultraviolet (UV) light excitation, which limits its tissue penetration depth and can be toxic to cells, because most of biomolecules have UV absorption. One solution to increase the excitation wavelength is to modify the conjugated structure of photoresponsive groups. However, the photoresponsive performance (e.g., the quantum yield of photoreaction) is uncertain and the required organic synthesis would also be time and labor consuming. An alternative solution is to take advantage of upconversion luminescence (UCL) systems, which can emit UV light upon visible or near-infrared light excitation, including rare earth-doped upconversion nanoparticles (UCNPs) and triplet-triplet annihilation upconversion (TTA-UC) systems.[4] The UV light emitted by UCL systems are further used to activate the photoresponsive groups. For example, Shi and coworkers developed a NIR light-trigged drug release system by coating UCNPs with azobenzene-modified mesoporous silica.[5] Li and coworkers synthesized a coumarin-modified prodrug that was further loaded into yolk-shell UCNPs to trigger the drug release with 980 nm light excitation.[6] However, the upconversion efficiency of UCNPs is very low (only about 0.1% for absolute quantum efficiency under irradiation condition of 150 W/cm$^2$).[4a] Therefore, a high excitation power is required when conducting in vitro or in vivo studies, which quickly increases the temperature around the irradiation area and is harmful to healthy tissues.

Another upconversion system, TTA-UC, has a higher upconversion efficiency (as high as 20%)[4a] compared with UCNPs. Previously, we reported a phototriggered targeting system using TTA-UCL as energy donors to activate the targeting function of (7-diethylaminocoumarin-4-yl)methyl (DEACM) modified c[R]GDfK with green light (530 nm) irradiation.[7] Han and coworkers further developed a TTA-UC system with a new pair of photosensitizer and annihilator, which allows red light to trigger drug release.[8] Both systems could be triggered with low-power-density LED light in vivo, indicating a more promising application prospect in medicine. However, the quantum yield of TTA-UCL is theoretically lower than 0.5 because the emission of one upconverted photon (UV light) requires absorption of two photons at longer wavelength (visible or NIR light).[4a] Moreover, TTA-UCL involves multi-step intramolecular and intermolecular energy transfer processes. Majority of absorbed energy will be consumed through unexpected ways, resulting in low UCL quantum efficiency and low photo-triggered drug release efficiency. Therefore, new strategies are highly desired for the development of highly efficient photoresponsive drug delivery systems with long wavelength excitation.

Photoresponsive drug delivery systems have shown great potential in spatiotemporal control of drug release. However, most of these systems require ultraviolet (UV) light excitation, which limits tissue penetration depth and can be toxic to cells. Thus, it is important to develop a photoactivation strategy that uses light at longer wavelengths than the absorption window of the photoresponsive groups with a high efficiency.

3. Summary

The present disclosure generally relates to various phototriggered drug release and photoreactions based on triplet-triplet energy transfer with light excitation at long wavelengths. In one aspect, the present invention is generally directed to a composition. In one set of embodiments, the composition comprises a photosensitizer, a cleavable moiety able to accept energy from the photosensitizer in the higher energy state to cause cleavage of the cleavable moiety, and a releasable moiety releasable from the composition upon cleavage of the cleavable moiety.

The composition, in yet another set of embodiments, comprises a carrier material comprising a photosensitizer, an active moiety, and a releasable moiety. In some embodiments, absorption of an incident photon by the photosensitizer causes energy transfer to the photosenstizer and then to the active moiety to cause a chemical reaction within the active moiety. In one set of embodiments, the composition comprises a photosensitizer able to absorb a photon to produce higher energy state, triplet-triplet energy transfer from the photosensitizer to a cleavable moiety able to cause cleavage of the cleavable moiety, and a releasable moiety releasable from the composition upon cleavage of the cleavable moiety. According to another set of embodiments, the composition comprises a photosensitizer able to directly sensitize a cleavable moiety via triplet-triplet transfer process (TTET). In one embodiment, the composition does not comprise an annihilator.

The present invention, in another aspect, is generally drawn to a method. In accordance with one set of embodiments, the method includes absorbing a photon in a photosensitizer, transferring energy from the photosensitizer directly to an active moiety via triplet-triplet energy transfer, producing an excited state of a cleavable moiety via triplet-triplet energy transfer, and causing a chemical reaction in the active moiety using the transferred energy.

The method, in another set of embodiments, includes applying, to a subject, a composition comprising a photosensitizer, a cleavable moiety able to accept triplet-triplet energy transfer from the photosensitizer to cause cleavage of the cleavable moiety, and applying light to at least a portion of the subject to cause cleavage of the cleavable moiety.

In still another set of embodiments, the method includes applying, to a subject, a composition comprising a photosensitizer, a cleavable moiety, and a carrier material, and applying light to the subject. In some cases, absorption of light by the photosensitizer causes energy transfer to the cleavable moiety to cause cleavage of the cleavable moiety.

In still another set of embodiments, the method includes applying, to a tumor in a subject, a composition comprising a photosensitizer, a cleavable moiety, and a carrier material, and applying light to at least a portion of the tumor, wherein absorption of light by the photosensitizer causes energy transfer to the cleavable moiety to cause cleavage of the cleavable moiety.

In another aspect, the present invention encompasses methods of making one or more of the embodiments described herein, for example, compositions comprising photosensitizers and a cleavable moiety. In still another aspect, the present invention encompasses methods of using one or more of the embodiments described herein, for example, compositions comprising photosensitizers and a cleavable moiety.

5. DETAILED DESCRIPTION

Figure 1:
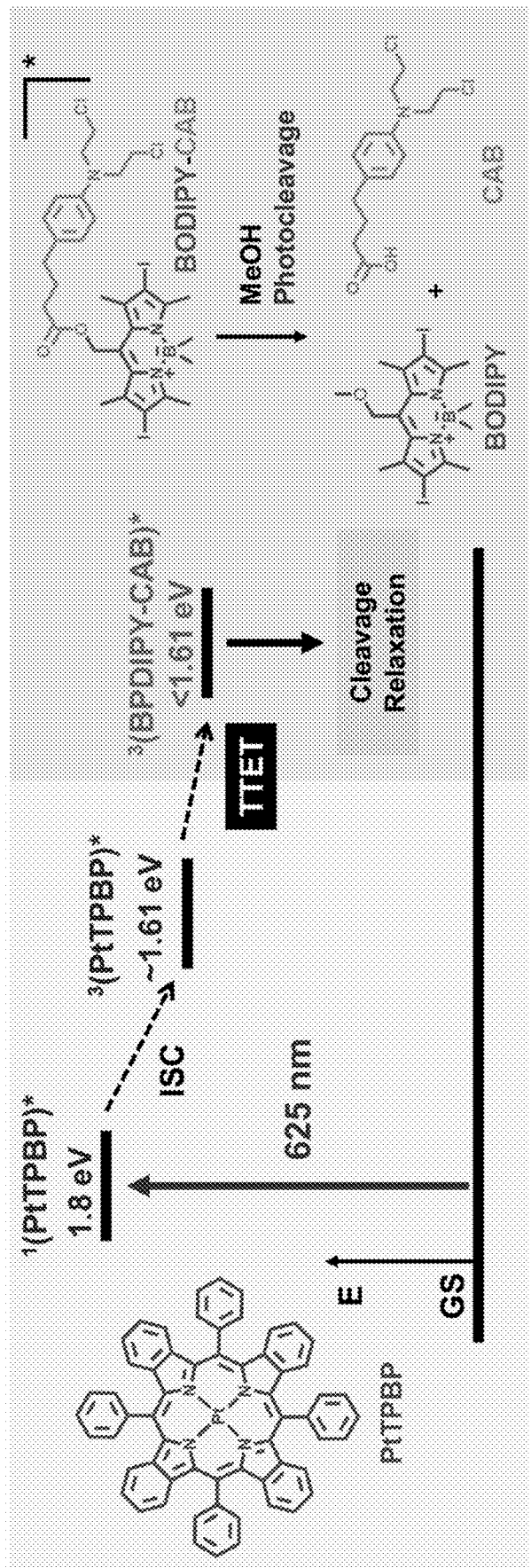
FIG. 1. Jablonski diagram of TTET from the photosensitizer (PtTPBP) to the prodrug (BODIPY-CAB). The excited state of BODIPY-CAB triggers the photocleavage of the prodrug to release the anticancer drug CAB. GS, ground state; ISC, intersystem crossing; TTET, triplet-triplet energy transfer.

The present disclosure generally relates to various photoreactions, including reactions generally based on triplet-triplet energy transfer process (TTET) from photosensitive and photocleavable groups. One aspect of the present invention is directed to systems and methods for absorbing energy (e.g., from a photon) in a photosensitizer, transferring that energy by triplet-triplet energy transfer to cleave a cleavable or other active moiety, for instance, in order to cause the release of a releasable moiety. In some cases, the photosensitizer and the cleavable moiety may be contained within a suitable carrier material, for example, a particle or a micelle. Such systems and methods may be used in a variety of applications, including various biological or physical applications. For example, such systems and methods may be useful for delivering drugs or other releasable moieties to regions of the body in a subject. Other aspects of the present invention are generally directed to methods for making or using such systems, kits including such systems, or the like.

In one embodiment, the disclosed method is based on the triplet-triplet energy transfer (TTET) process between photosensitizers and photocleavable groups. Compared with conventional triplet-triplet annihilation upconversion (TTA-UC)-based photocleavage, our strategy simplifies the energy transfer process and excites photocleavable groups without annihilators, which improves the photocleavage efficiency. To prove this concept, we designed a boron-dipyrromethene (BODIPY)-based prodrug and chose platinum (II) tetraphenyltetrabenzoporphyrin (PtTPBP or PtTPTBP) as photosensitizers. We demonstrate that the red light at 625 nm triggered the drug release at a low irradiance over a short period.

The study is the first example of developing phototriggered drug delivery systems based on TTET process, which provides a promising way to design long-wavelength light-triggered systems for practical biomedical applications.

It should be understood that, as is known to those of ordinary skill in the art, the term "triplet" generally refers to the electronic state of a molecule, not to the number of electrons that are present within the molecule. For example, in a triplet state, the molecule may have unpaired electrons present such that the net spin the molecule has is 1. Absorption of energy by a molecule, e.g., through absorption of a photon, may result in an electron from the molecule being "raised" from a lower energy state (or shell) to a higher energy state (or shell), which may alter the net spin of the molecule, while emission or transfer of that energy may allow a higher-energy electron to return to a lower state.

For example, in some cases, the energy from the triplet state of the photosensitizer may be transferred to a cleavable moiety. A variety of mechanisms may be involved in the transfer of such energy, such as triplet-triplet energy transfer (TTET). For instance, triplet-triplet energy transfer may be accomplished through the exchange of electrons that carry different spin and energy, e.g., between two molecules (such as between the cleavable moiety and a photosensitizer). The cleavable moiety may then be cleaved as a result of the energy from the photosensitizer. The energy transfer to the cleavable moiety may occur through a variety of processes.

Cleavage of the cleavable moiety can cause breakage of one or more bonds (e.g., covalent bonds) within or linked to the cleavable moiety. In some cases, cleavage of the cleavable moiety may cause a portion of the moiety to become separated or released, e.g., as a releasable moiety. Thus, in such a fashion, absorption of a photon (e.g., via a photosensitizer) may produce a chain of events that results in the release of releasable moiety. Accordingly, by controlling the incident light, the release of releasable moiety can be controlled as desired. However, it should be understood that a releasable moiety is not required, for example, cleavage of the cleavable moiety may result in other chemical or structural changes within the cleavable moiety. In addition, it should be understood that the energy may be transferred to other active moieties instead of a cleavable moiety, e.g., the energy may result in photoisomerization, rearrangement, photocycloaddition, or other chemical reactions.

Thus, in one set of embodiments, a composition comprising a photosensitizer and a cleavable moiety (or other active moiety) may be applied to a region (e.g., within a sample, within a subject, etc.), and light applied to the region (or at least a portion of the region) in order to cause cleavage of the cleavable moiety, for example, to cause a chemical change, to release a releasable moiety, or the like. As mentioned, other active moieties may also be used. For example, if the active moiety is a cleavable moiety, the releasable moiety may be a drug, and light may be applied to thereby cause release of the drug. In one embodiment, the transferred energy causes photoreaction of the active moiety (e.g., photoisomerization, rearrangement, photocleavage, or other chemical reactions). In one embodiment, the photoreaction further triggers the structural or compositional change of the carrier material containing the composition. In certain embodiments, the encapsulated drugs or other molecules/objects can be released. As another non-limiting example, the releasable moiety can be a tracer (for example, a radioactive tracer, an inert molecule, a detectable entity, etc.) that can be introduced to a system (e.g., a biological system such as a cell or an organism, or a non-biological system such as a polymer), and the tracer released at an appropriate time (e.g., through applying light), for instance, instead of being instantly released upon administration or incorporation of the composition. The tracer may then be detected using any suitable technique, e.g., fluorescence, radioactivity, biological assay, chemical or enzymatic activity, etc.

In some cases, components such as the photosensitizer and/or the cleavable moiety may be contained within a suitable carrier material using physical encapsulation or chemical conjugation. In some cases, the components are on the surface of the carrier material. In some cases, the components are part of the carrier material. In some cases, the carrier material may hold the photosensitizer and/or the cleavable moiety in close proximity to each other, e.g., to allow for electron and/or photon transfers to occur as discussed herein. For example, in one embodiment, the photosensitizer and/or the cleavable moiety may be contained within a particle, such as a microparticle or a nanoparticle. In some cases, the particle may contain an environment (e.g., a hydrophobic or nonpolar environment), for instance, to keep the photosensitizer or the cleavable moiety in close proximity, to facilitate transfer of electrons and/or photons, etc.

For instance, in one set of embodiments, the composition includes a photosensitizer. The photosensitizer can be any composition that is able to absorb a photon to produce a higher energy state. The energy may be transferrable to the cleavable moiety. In some cases, the photosensitizer is able to absorb a wavelength of visible light, i.e., about 390 to about 700 nm. However, in some instances, infrared light (e.g., about 650 nm to about 1350 nm, or about 700 nm to about 1200 nm, etc.) may be absorbed by the photosensitizer.

As non-limiting examples, the photosensitizer may have an excitation wavelength of at least about 600 nm-650 nm, at least about 650 nm-700 nm, at least about 750 nm-800 nm, at least about 800 nm-850 nm, at least about 850 nm-900 nm, at least about 900 nm-950 nm, at least about 950 nm-1000 nm, at least about 1000 nm-1100 nm, at least about 1100 nm-1200 nm. It should be understood that the photosensitizer can be excited by light of a single wavelength (e.g., monochromatic light, such as would be supplied by a laser), or by light of different wavelengths (e.g., from a light source producing a spectrum of wavelengths).

The photosensitizer is a fluorophore in some embodiments. Non-limiting examples of transition metals useful in photosensitizers include Ir, Pd, Pt, Ru, or Zn. A variety of triplet photosensitizers are known to those of ordinary skill in the art; many of these are commercially available. In one embodiment, the photosensitizer is porphyrin or a porphyrin derivative, e.g., a transition metal-porphyrin such as a Pt porphyrin or a Pd porphyrin. Specific non-limiting examples of photosensitizers include platinum (II) tetraphenyltetrabenzoporphyrin (PtTPBP), palladium(II) tetraphenyltetrabenzoporphyrin (PdTPBP), meso-tetraphenylltetrabenzoporphyrin (PdPh4TBP) or palladium(II) meso-tetraphenyl-octamethoxide-tetranaphtholporphyrin [PdPh4MeO8TNP]. Non-limiting examples of metal-free molecules used as photosensitizers include some boron-dipyrromethene (BODIPY) derivatives and fullerene derivatives.

In some cases, the transfer of energy to the active moiety results in the cleavage of a bond within or linked to the cleavable moiety, and/or within or linked to a different portion of a cleavable moiety. Cleavage of the bond, in some embodiments, can cause the release of a portion of the cleavable moiety, e.g., as a releasable moiety. However, it should be understood that in other embodiments, the cleavage of a single bond does not necessarily require the release of a releasable moiety, for instance, if more than one bond connects portions of the molecule together. In addition, in some embodiments, transfer of energy to the active moiety may result in other chemical reactions within the active moiety, not necessarily leading to the cleavage of a cleavable bond. If present, a releasable moiety may be any suitable moiety that can be released, e.g., during cleavage (including photocleavage). The releasable moiety can include a portion of the cleavable entity. Different releasable moieties can be used in various embodiments, depending on the application. For example, the releasable moiety may include a drug, a tracer (e.g., a fluorescent or radioactive compound), a caged species, a peptide or protein, a small molecule (e.g., having a molecular weight of less than about 1 kDa or about 2 kDa), or the like. In some cases, the exact form of the releasable moiety is not critical, e.g., if it is attached through a cleavable bond of a cleavable moiety that itself is cleaved as discussed above; cleavage of the cleavable bond may thereby cause separation of the releasable moiety, regardless of the exact composition of the releasable moiety.

As non-limiting examples, in one set of embodiments, the releasable moiety can include an anti-angiogenesis drug, such as TNP-470 or Combretastatin A4. In another set of embodiments, the releasable moiety may include an anti-inflammatory drug, such as dexamethasone. In yet another set of embodiments, the releasable moiety includes an anticancer drug and/or a chemotherapy drug, such as chlorambucil, doxorubicin, topotecan, or verteporfin. In yet another set of embodiments, the releasable moiety may include fluorescent proteins, such as GFP or YFP. In still another set of embodiments, the releasable moiety can include fluorescent compounds, such as fluorescein, rhodamine, or calcein. In still another set of embodiments, the releasable moiety includes a peptide or a protein, such as an RGD peptide. In another set of embodiments, the releasable moiety may include a radioactive atom.

In some embodiments, the photosensitizer, the active moiety (e.g., a cleavable moiety), and/or the releasable moiety (if present) are contained within a suitable carrier material. The carrier material may hold some or all of these in close proximity to each other (e.g., as discussed above). In some cases, the carrier material may create an environment favorable for compounds such as those discussed herein to be fluorescent. For example, the carrier material may create an aqueous environment, a hydrophobic environment, a polar or non-polar environment, etc. In some cases, the carrier material creates an environment that repels water.

In one set of embodiments, the carrier material is formed from a polymer. Any suitable polymer can be used. Examples of polymers include, but are not limited to, polylactic acid, polyglycolic acid, polyethylene oxide, polystyrene, polyethylene, polypropylene, etc. In some embodiments, the polymer may be biodegradable or biocompatible, e.g., for use in various medical or biological applications. In some cases, more than one polymer can be used, and the polymers may be physically blended together and/or chemically combined, e.g., as in a copolymer. As a non-limiting example, the carrier material may include a copolymer such as poly(D,L-lactic acid)-poly(ethylene oxide).

However, it should be understood that the carrier material needs not be limited to polymeric materials. For example, in other embodiments, the carrier material can include silica, ceramics, or other materials.

The carrier material can be present in any suitable form. For example, the carrier material can be present as a film, as a block of material, as particles, as a micelle, or the like. In some cases, components such as the photosensitizer, the active moiety, and/or the releasable moiety may be added or chemically conjugated to the carrier material during and/or after formation of the carrier material. The carrier material can be formed using any suitable techniques; for example, techniques for producing polymers, silica gels, ceramics, etc. are known to those of ordinary skill in the art.

If the carrier material is present as particles, the particles may be spherical or nonspherical, and may have any suitable diameter. For instance, the particles may have an average diameter of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, less than about 1 micrometer, less than about 500 nm, less than about 300 nm, less than about 100 nm, less than about 50 nm, less than about 30 nm, less than about 10 nm, etc. The average diameter of a nonspherical particle may be taken as the volume of a perfect sphere having the same volume of the particle. If the carrier material is present as a film, the film can have any cross-sectional thickness. For example, the film may have an average thickness of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, less than about 1 micrometer, less than about 500 nm, less than about 300 nm, less than about 100 nm, less than about 50 nm, less than about 30 nm, less than about 10 nm, etc.

The carrier material may also comprise one or more polymeric micelles. The polymer micelles may have any suitable average diameter. For example, the micelles can have an average diameter of less than about 1 mm, less than about 500 micrometers, less than about 300 micrometers, less than about 100 micrometers, less than about 50 micrometers, less than about 30 micrometers, less than about 10 micrometers, less than about 5 micrometers, less than about 3 micrometers, less than about 1 micrometer, less than about 500 nm, less than about 300 nm, less than about 100 nm, less than about 50 nm, less than about 30 nm, less than about 10 nm, etc.

As mentioned, compositions such as those discussed herein may be used in a wide variety of applications, including biological and medical applications, as well as non-biological or non-medical applications. As a non-limiting example, in one set of embodiments, a composition as discussed herein may be applied to a subject. The subject may be human or non-human. For example, the subject may be a rat, mouse, rabbit, goat, cat, dog, or the like. The composition can also be applied to any suitable sample, e.g., a biological sample, a physical sample, a chemical sample, or the like.

Light may be applied to the composition to cause release of the releasable moiety, if present. The light may be monochromatic light (e.g., laser or coherent light), or the light may be nonmonochromatic or noncoherent in some embodiments. The light may have any suitable frequency, e.g., including the frequencies discussed herein.

In one set of embodiments, the composition is applied to a subject to treat a tumor.

The composition may be applied directly to the tumor, and/or applied systemically to the body of the subject such that at least some of the composition is able to travel to the tumor (e.g., via the blood) such that light can be applied to the tumor (or portion thereof), e.g., to cause release of a releasable moiety for diagnosing and/or treating the tumor. The composition can include, for example, an anti-angiogenesis drug, an anti-inflammatory drug, a radioactive species, an anticancer drug and/or a chemotherapy drug, and light may be applied to the tumor to cause release. Such application may be targeted, e.g., by applying light directly to the tumor (or at least a portion thereof); thus, release elsewhere within the subject may be minimized by not applying light to other places. In such a fashion, release of a drug (or other suitable release moiety) may be controlled or localized at or near the tumor by applying light directly to the tumor (or portion thereof), or at least proximate the tumor. In some cases, more than one composition may be present.

Other portions of a subject may also be treated in various embodiments. For instance, the composition may be applied directly to a specific location within the subject, or applied systemically to the subject such that at least some of the composition is able to travel to a location where light is to be applied. For instance, the composition may be applied to the skin, eye, body cavity (or to the blood) and light applied to a portion of the skin, eye, body cavity or the blood to cause local release of a releasable moiety.

In various aspects, the compositions described herein can be administered by any suitable method, e.g., contained in a solution or suspension, such as inhalation solutions, local instillations, eye drops, intranasal introductions, an ointment for epicutaneous applications, intravenous solutions, injection solutions (e.g., subcutaneous, or intravenous), or suppositories. In one set of embodiments, the composition is introduced parenterally or topically. For instance, the composition may be contained within a cream, gel, or ointment applied to the skin. In some embodiments, the composition can be applied one or more times a day, by one or more administrations per day, by fewer than one time per day, or by continuous administration, etc., until a desired therapeutic effect is achieved.

As mentioned, certain aspects of the present invention provide methods of administering any composition of the present invention to a subject. When administered, the compositions of the invention are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the subject. Any of the compositions of the present invention may be administered to the subject in a therapeutically effective dose. A "therapeutically effective" amount as used herein means that amount necessary to delay the onset of, inhibit the progression of, halt altogether the onset or progression of, diagnose a particular condition being treated, or otherwise achieve a medically desirable result. When administered to a subject, effective amounts will depend on the particular condition being treated and the desired outcome. A therapeutically effective dose may be determined by those of ordinary skill in the art, for instance, employing factors such as those further described below and using no more than routine experimentation.

Any medically acceptable method may be used to administer the composition to the subject. The administration may be localized (i.e., to a particular region, physiological system, tissue, organ, or cell type) or systemic, depending on the condition to be treated. For example, the composition may be administered orally, vaginally, rectally, buccally, pulmonary, topically, nasally, transdermally, through parenteral injection or implantation, via surgical administration, or any other methods of administration. Examples of parenteral modalities that can be used with the invention include intravenous, intradermal, subcutaneous, intracavity, intramuscular, intraperitoneal, epidural, or intrathecal. Examples of implantation modalities include any implantable or injectable drug delivery systems. Use of an implant may be particularly suitable in some embodiments of the invention. The implant containing the composition may be constructed and arranged to remain within the body for at least 2-4 hours, 4-12 hours, 12-24 hours, 24-48 hours, 1-7 days, 7-15 days, for at least 30 or 45 days, and preferably at least 60 or 90 days, or even longer in some cases. Long-term release implants are well known to those of ordinary skill in the art.

In certain embodiments of the invention, a composition can be combined with a suitable pharmaceutically acceptable carrier, for example, as incorporated into a liposome, incorporated into a polymer release system, or suspended in a liquid, e.g., in a dissolved form, or a colloidal form, or a micellar form. In general, pharmaceutically acceptable carriers suitable for use in the invention are well-known to those of ordinary skill in the art. A pharmaceutically acceptable carrier may include non-toxic material that does not significantly interfere with the effectiveness of the biological activity of the active compound(s) to be administered, but is used as a formulation ingredient, for example, to stabilize or protect the active compound(s) within the composition before use. The carrier may be organic or inorganic, and may be natural or synthetic, with which one or more active compounds of the invention are combined to facilitate the application of the composition. The carrier may be either soluble or insoluble, depending on the application.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions.

The following examples are intended to illustrate certain embodiments of the present invention, but do not exemplify the full scope of the invention.

6. EXAMPLES

Recently, a series of new photocleavable groups based on meso-methyl BODIPY have been reported by Winter and coworkers.[9] These BODIPY molecules could be cleaved to release leaving groups when they are excited to their singlet or triplet excited state with green light. Here, a prodrug was synthesized by modifying anticancer drug (chlorambucil, CAB) with the meso-methyl BODIPY group. As the prodrug can release the leaving group (free drug) at its triplet excited state, we hypothesize that a photosensitizer (platinum (II) tetraphenyltetrabenzoporphyrin, PtTPBP) with higher triplet excited state energy (~1.61 eV) than that of the BODIPY prodrug (calculated to be 1.52 eV for BODIPY-CAB) directly sensitize the prodrug to its triplet excited state through the triplet to triplet energy transfer (TTET) process (FIG. 1) to achieve the photocleavage reaction and drug release. Since PtTPBP can be excited by a red light (wavelength at 625 nm), which means red light irradiation can cleave BODIPY prodrug through TTET process instead of green light (directly excite BODIPY to singlet excited state to achieve the photocleavage reaction). It should also be highlighted that the energy transfer process proposed here is much simpler than the combination of UCL and photocleavage mentioned above. Besides, the long-lived triplet excited state of the prodrug will provide longer time for cleavage than the singlet excited state of the prodrug, which means that more efficient photocleavage and drug release are expected.

Figure 2:
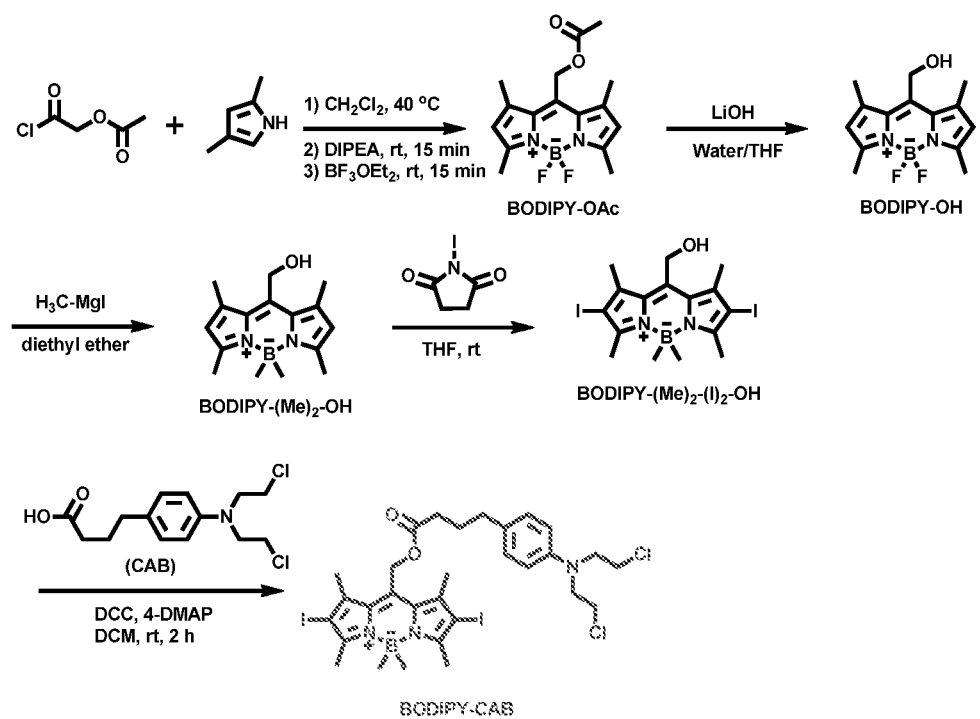
FIG. 2. The synthesis route of the prodrug (BODIPY-CAB).
Figure 3:
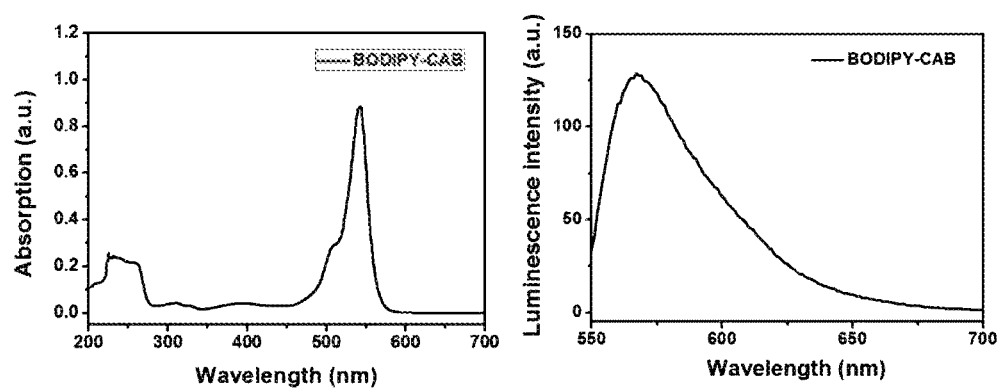
FIG. 3. Absorption and emission spectra of BODIPY-CAB ($1\times10^{-5}$ M) in dichloromethane. The excitation wavelength for the emission spectrum was 543 nm.
Figure 4:
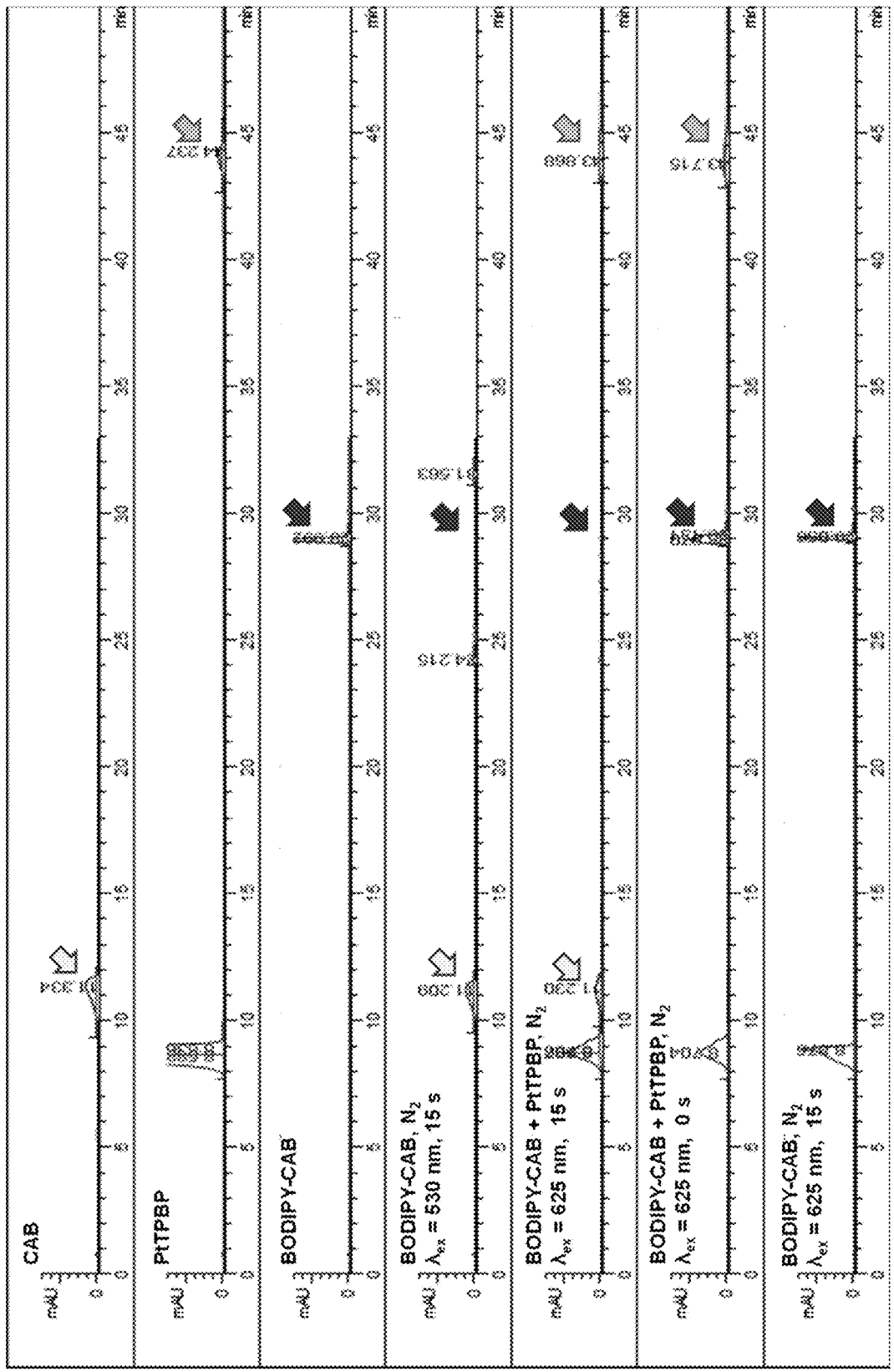
FIG. 4. HPLC spectra of CAB ($10^{-4}$ M), PtTPBP ($10^{-5}$ M), BODIPY-CAB ($10^{-4}$ M), BODIPY-CAB ($10^{-4}$ M) with 530 nm irradiation (44 mW/cm$^2$) for 15 s under N$_2$ atmosphere, the mixture of BODIPY-CAB ($10^{-4}$ M) and PtTPBP ($10^{-5}$ M) with 625 nm irradiation (44 mW/cm$^2$) for 15 s under N$_2$ atmosphere, the mixture of BODIPY-CAB ($10^{-4}$ M) and PtTPBP ($10^{-5}$ M) without irradiation under N$_2$ atmosphere, and BODIPY-CAB ($10^{-4}$ M) with 625 nm irradiation (44 mW/cm$^2$) for 15 s under N$_2$ atmosphere. The detection wavelength was 260 nm. A small amount of toluene, whose peak was located at ~8.7 min, was used to increase the solubility of PtTPBP. The yellow arrows indicate the signal of CAB; the red arrows indicate the signal of BODIPY-CAB; and the green arrows indicate the signal of PtTPBP.

The synthesis route of the prodrug (BODIPY-CAB) is shown in FIG. 2. The intermediates and the final product were characterized by proton nuclear magnetic resonance ($^1$H NMR) spectra (FIG. 12-FIG. 15). The absorption and emission peaks of BODIPY-CAB were located at the wavelength of 543 nm and 567 nm, respectively (FIG. 3). To confirm whether the BODIPY prodrug could be sensitized by PtTPBP and could further be cleaved to release the drug, high performance liquid chromatography (HPLC) was utilized to monitor the generation of CAB. As shown in FIG. 4, a new peak at ~11.2 min, which is the peak of CAB, was appeared after the BODIPY-CAB was irradiated with 530 nm light for 15 sec. The result indicates direct excitation of BODIPY-CAB by green light leads to the release of CAB. After addition of photosensitizer PtTPBP, the mixture solution of PtTPBP and BODIPY-CAB was irradiated with 625 nm light for 15 sec. As expected, the new peak located at ~11.2 min was appeared too. On the contrary, the mixture solution that was not irradiated or irradiated at 625 nm in the absence of photosensitizer PtTPBP did not generate CAB. The results demonstrate that the photocleavage of BODIPY-CAB can be activated at 625 nm through the TTET process using PtTPBP as photosensitizer.

Figure 5:
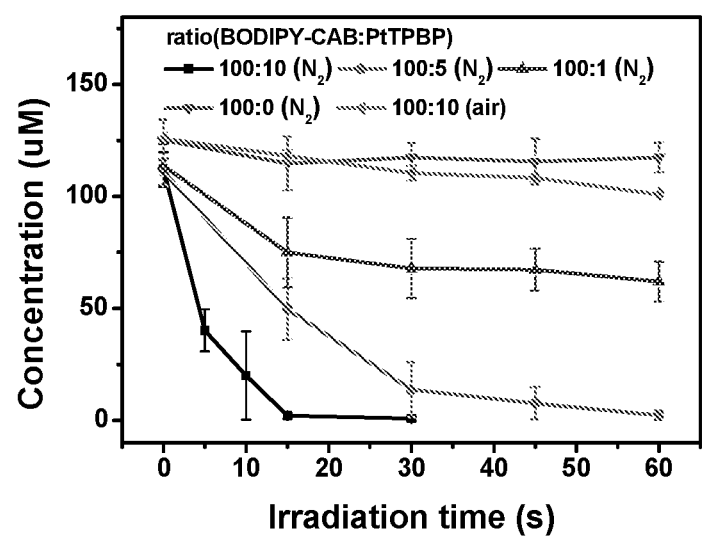
FIG. 5. Photocleavage rate of the prodrug (BODIPY-CAB), as determined by HPLC (detected at 540 nm), after irradiation with 625 nm LED light at 44 mW/cm$^2$. The mixed solution of BODIPY-CAB ($10^{-4}$ M) and PtTPBP ($10^{-5}$ M, $5\times10$ M, 10, M or 0 M) was protected under nitrogen (N$_2$) or exposed in the air, and then irradiated for different time periods in the mixed solvents of dichloromethane (DCM) and methanol (1:9, v/v). The solution (50 μL) was then analyzed by HPLC to measure the concentration of BODIPY-CAB. Data are means±SD, n=3.
Figure 6:
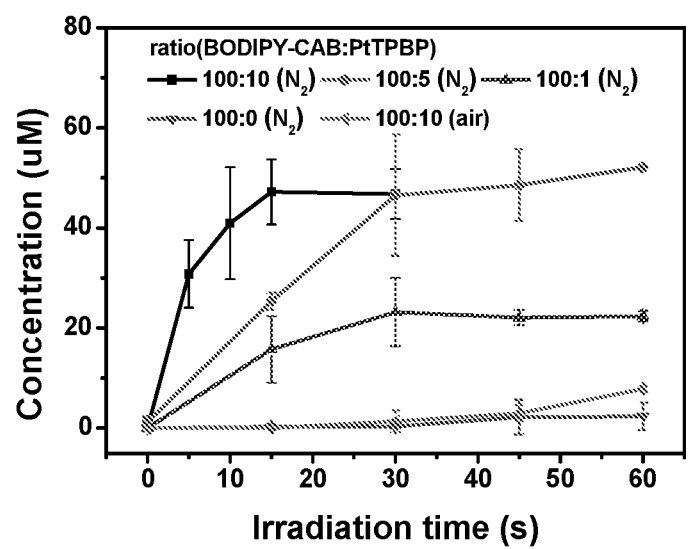
FIG. 6. Photorelease of the free drug (CAB), as determined by HPLC (detected at 260 nm), after irradiation with 625 nm LED light at 44 mW/cm$^2$. The mixed solution of BODIPY-CAB ($10^{-4}$ M) and PtTPBP ($10^{1}$ M, $5\times10^{-6}$ M, $10^{-6}$ M or 0 M) was protected under nitrogen (N$_2$) or exposed in the air, and then irradiated for different time periods in the mixed solvents of dichloromethane (DCM) and methanol (1:9, v/v). The solution (50 μL) was then analyzed by HPLC to measure the concentration of CAB. Data are means f SD, n=3.

Furthermore, the photocleavage of BODIPY-CAB was investigated with different ratios of BODIPY-CAB and PtTPBP upon 625 nm light irradiation. As shown in FIGS. 5 and 6, when the ratio of BODIPY-CAB and PtTPBP was 100:10, the prodrug was almost cleaved completely after the irradiation for 15 s and released 41.7% of the free drug CAB. When the concentration of photosensitizer was decreased, the photocleavage of BODIPY-CAB slowed down. At the ratio of BODIPY-CAB and PtTPBP being 100:1, about half amount of the prodrug (59.6%) was remained in the solution after the irradiation for 30 s. Moreover, as $O_2$ can quench the triplet excited state of PtTPBP, the prodrug cannot be cleaved efficiently in the presence of $O_2$. The photocleavage performed in the air atmosphere showed the dramatically deceased rate of photocleavage and photorelease (FIGS. 5 and 6). These results indicated that the ratio of PtTPBP could control the reaction rate of the photocleavage and the triplet excited state of PtTPBP played an essential role for the photocleavage.

Figure 7:
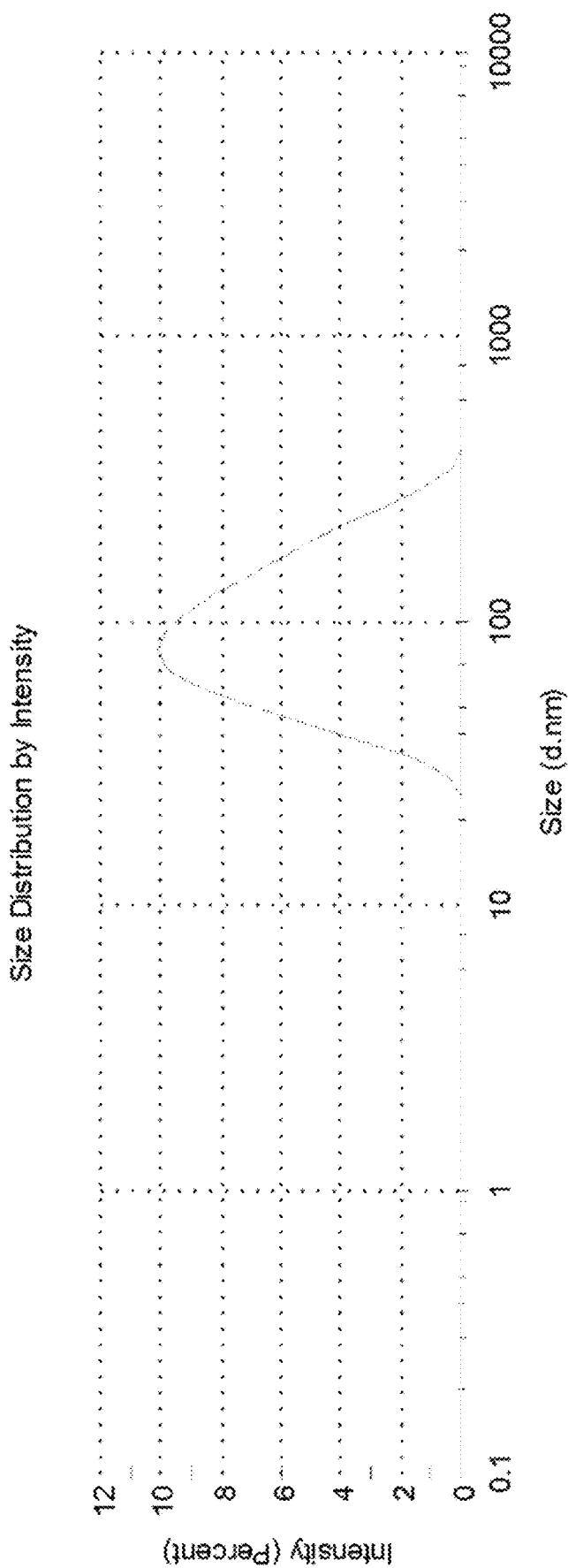
FIG. 7. Dynamic light scattering (DLS) analysis of BC&Pt@PLA-PEG-cRGDfK polymeric micelles. The average size is 124.7 nm with a polydispersity of 0.196.
Figure 8:
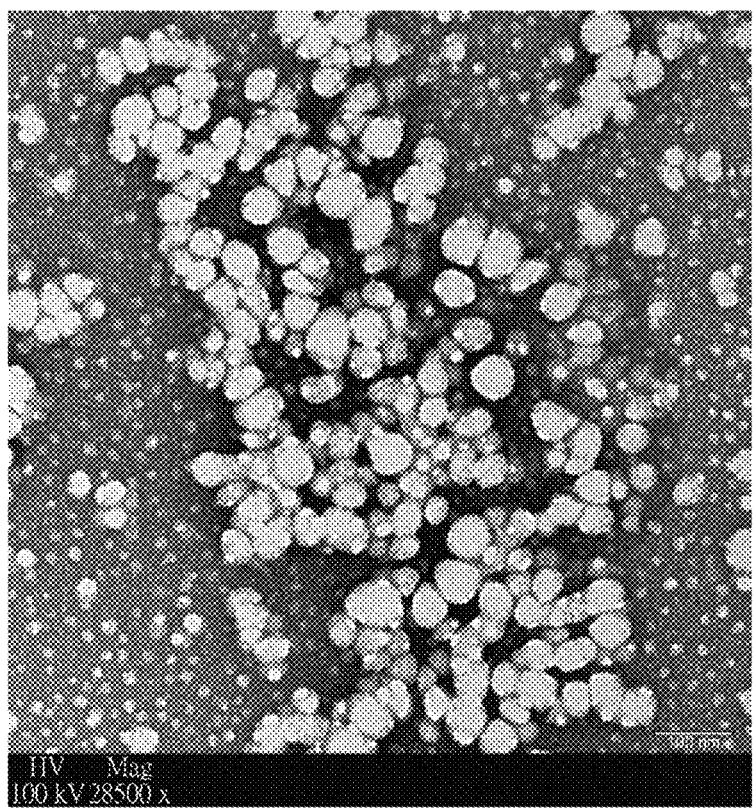
FIG. 8. Transmission electron microscopy (TEM) image of BC&Pt@PLA-PEG-cRGDfK polymeric micelles.
Figure 9:
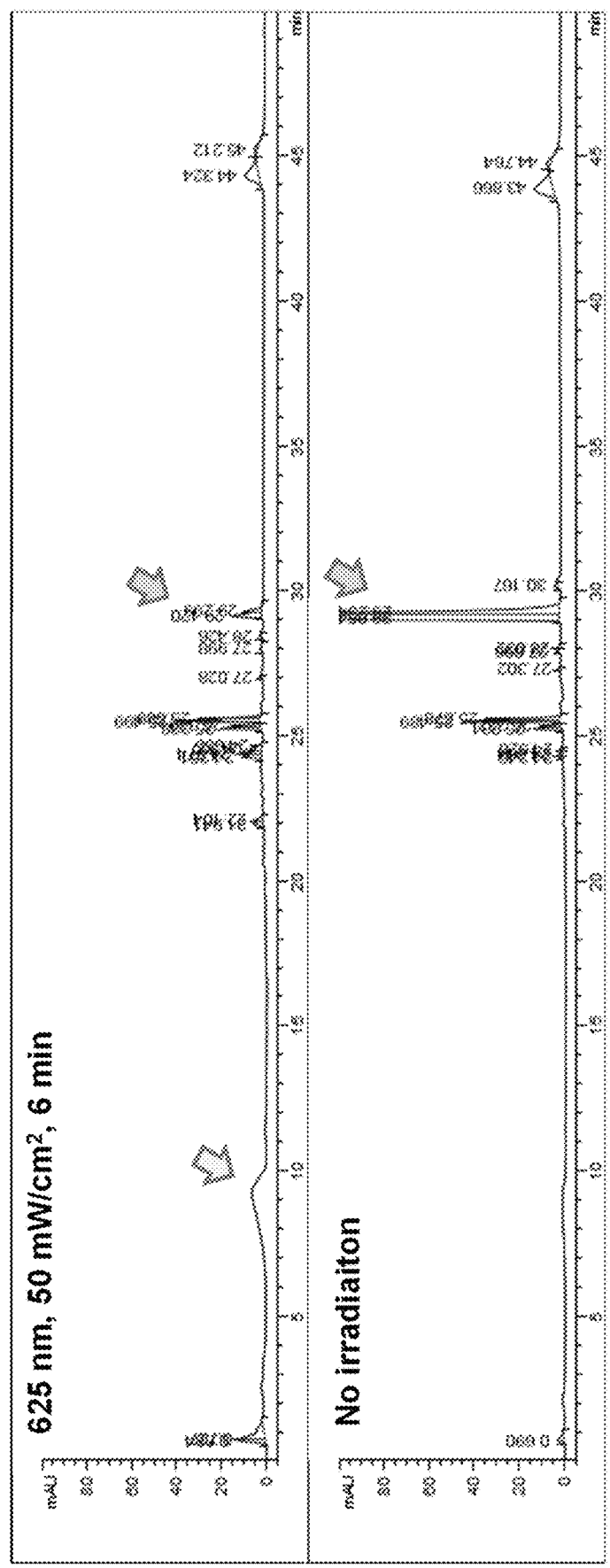
FIG. 9. High-performance liquid chromatography (HPLC) spectra of BC&Pt@PLA-PEG-cRGDfK polymeric micelles before and after 625 nm light irradiation (44 mW/cm$^2$, 6 min). The green arrows indicate the signal of BODIPY-CAB and the yellow arrow indicates the signal of CAB.

To increase the water solubility of the TTET-based phototriggered drug release system, the prodrug and PtTPBP were co-encapsulated in poly(lactic acid)-poly(ethylene oxide) (PLA-PEG) polymeric micelles through the flash precipitation method. The polymeric micelles were functionalized with the targeting peptide cyclo-(RGDfK) (BC&Pt@PLA-PEG-cRGDfK) to increase the nanoparticle accumulation in tumors. The morphology and size distribution of the micelles were analyzed by dynamic light scattering (DLS) and transmission electron microscopy (TEM) (FIGS. 7 and 8), which showed well-dispersed spherical nanoparticles and an average size of 124.7 nm with a polydispersity of 0.196. The photorelease of free drugs from the polymeric micelles upon light irradiation was analyzed by HPLC. As shown in FIG. 9, after the irradiation at 625 nm, the peak of prodrug decreases and a new peak of CAB appears, indicating that the photocleavage of prodrug can generate free drug CAB in the polymeric micelles.

Figure 10:
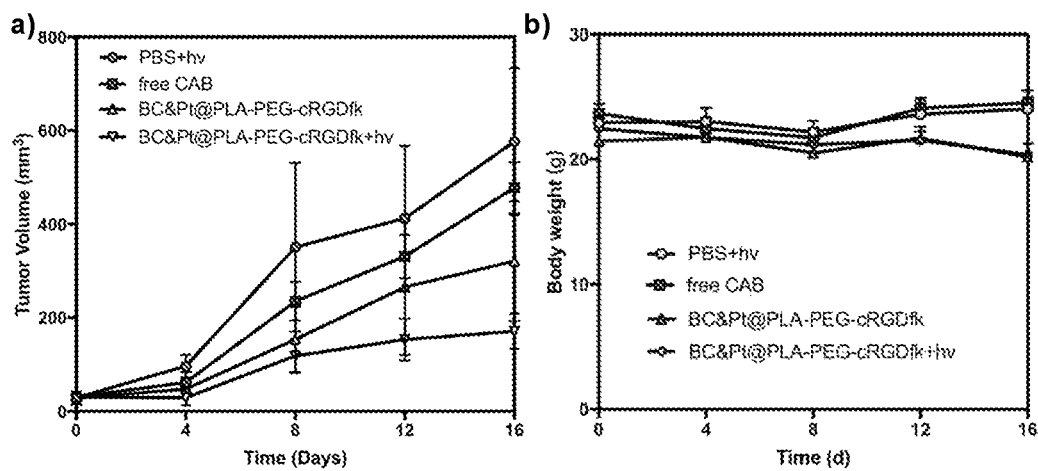
FIG. 10. a) Tumor volume and b) body weight of the 4T1 tumor-bearing mice. n=3.
Figure 11:
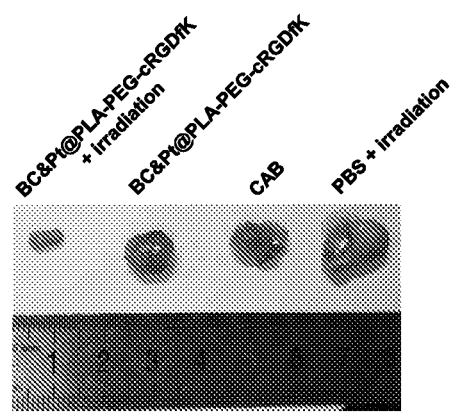
FIG. 11. Photograph of the tumors excised from the mice treated with different formulations.
Figure 12:
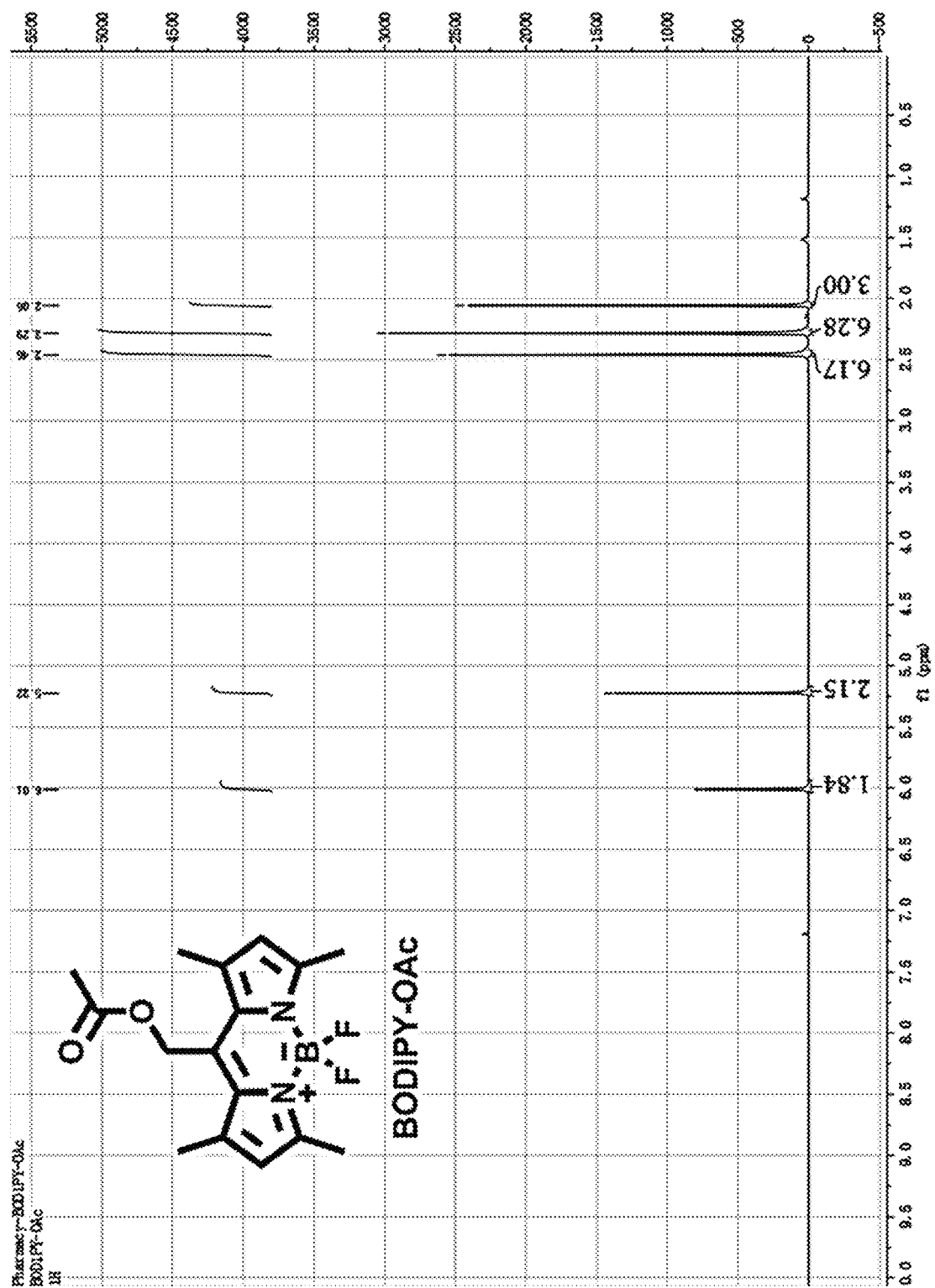
FIG. 12. $^1$H NMR spectrum of BODIPY-OAc.
Figure 13:
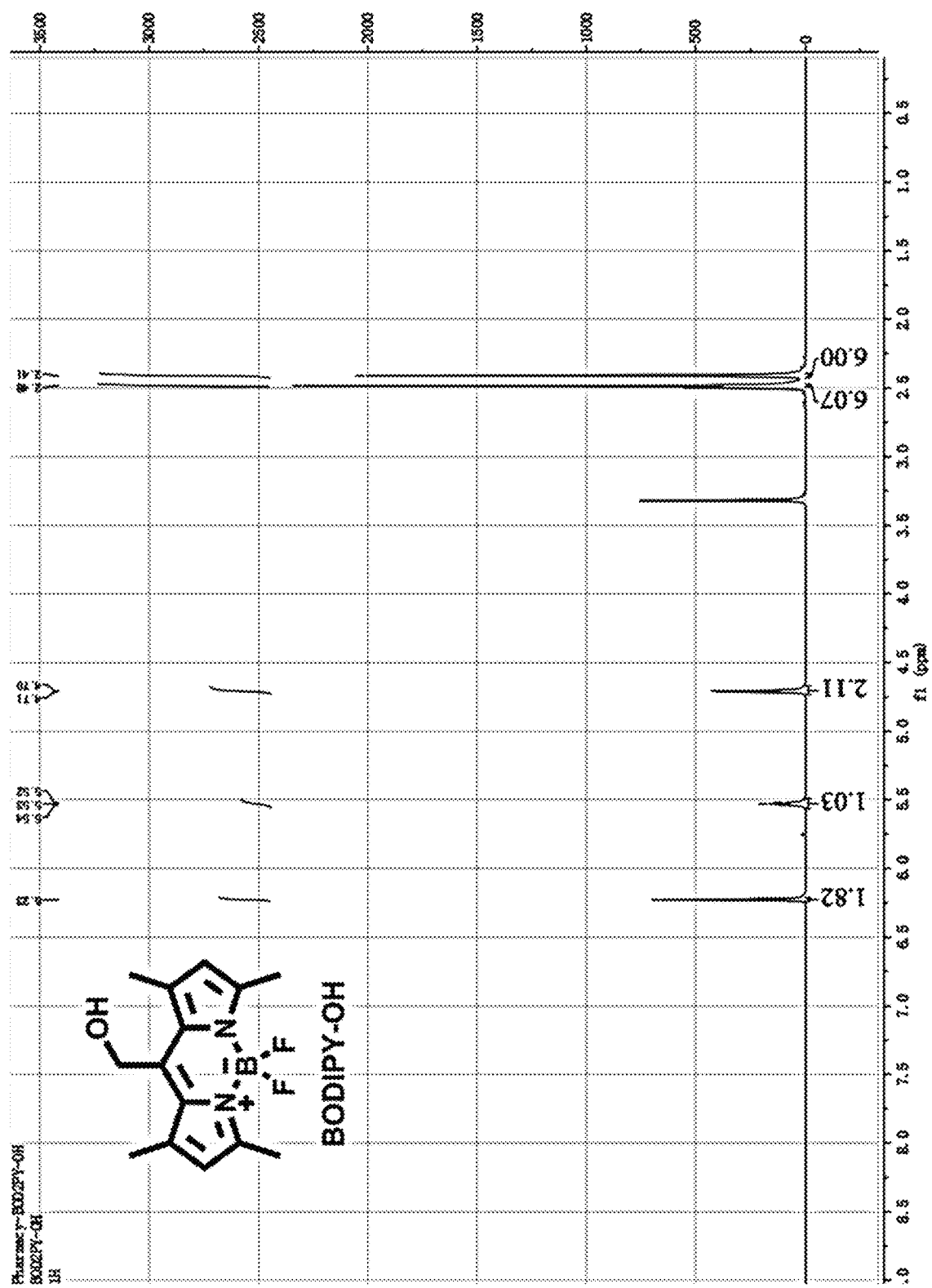
FIG. 13. $^1$H NMR spectrum of BODIPY-OH.
Figure 14:
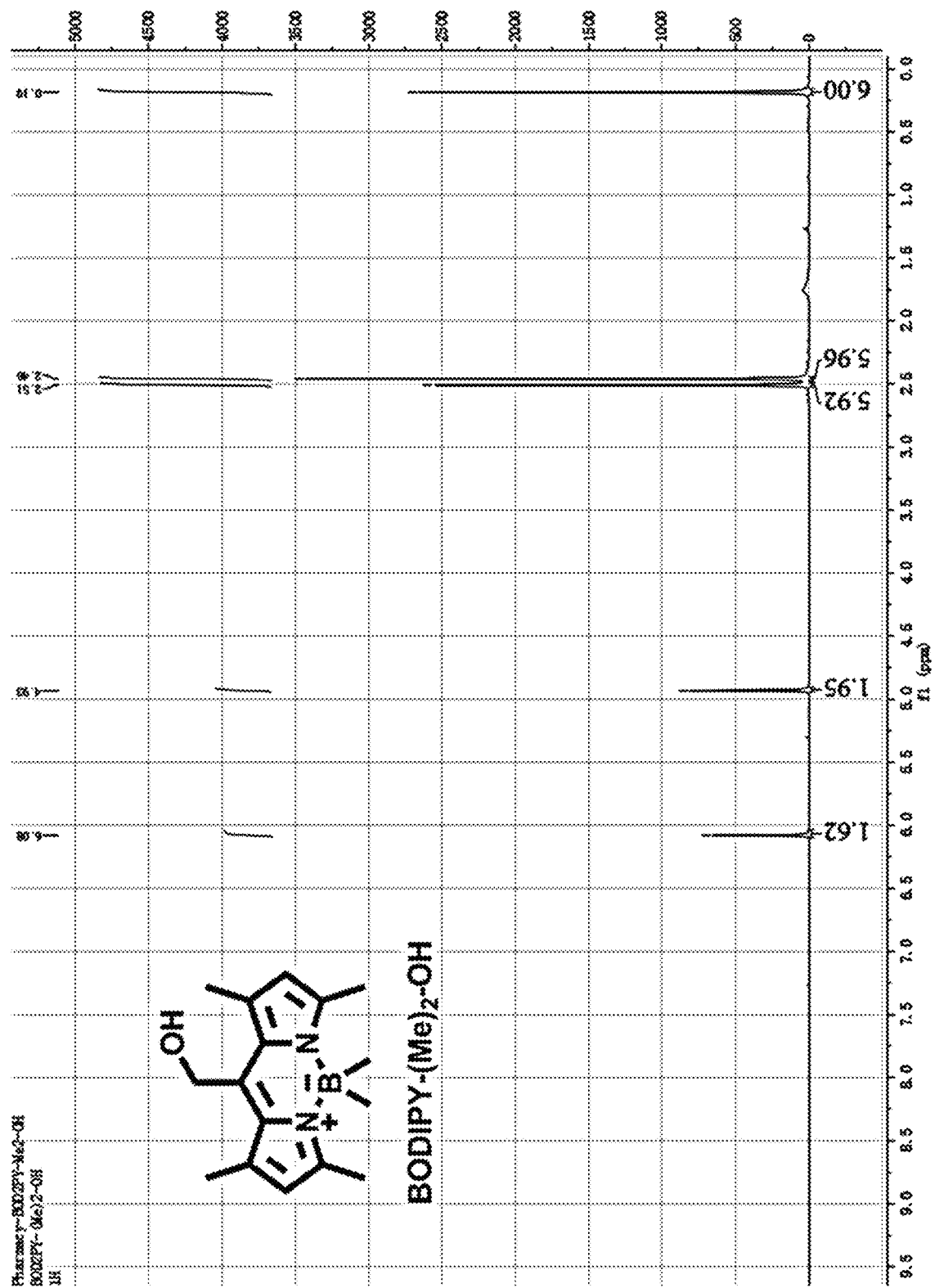
FIG. 14. $^1$H NMR spectrum of BODIPY-(Me)$_2$-OH.
Figure 15:
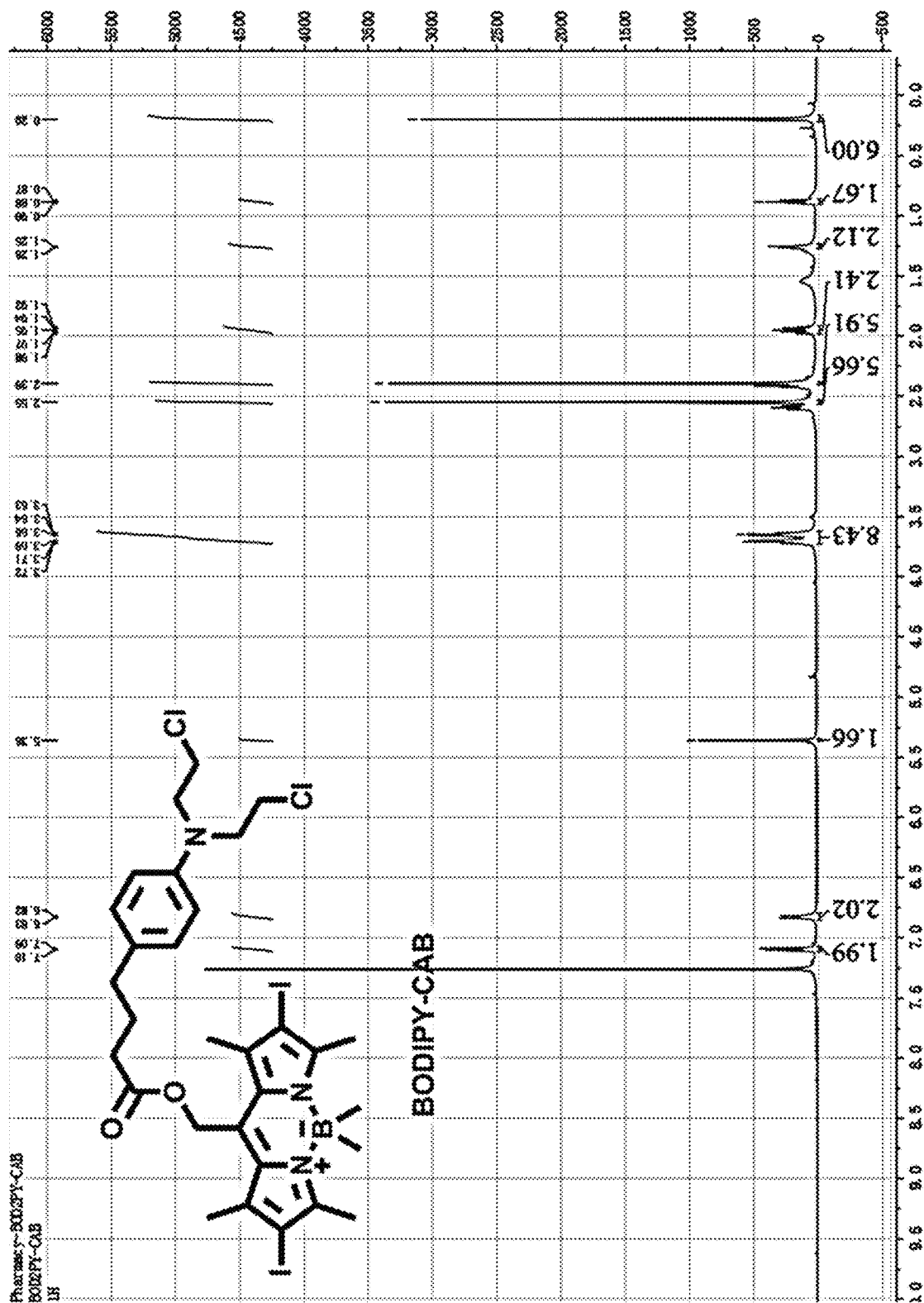
FIG. 15. $^1$H NMR spectrum of BODIPY-CAB.

To evaluate the in vivo therapeutic effect, 4T1 murine mammary carcinoma-bearing mice (subcutaneous xenograft tumor model, seven weeks) were intravenously injected with the four different formulations, separately: PBS+light irradiation; CAB only; BC&Pt@PLA-PEG-cRGDfK only; BC&Pt@PLA-PEG-cRGDfK+light irradiation. The CAB dose is 9.1 mg/kg per mouse. All treatments were performed every two days for 14 days. For the light irradiation groups, the mouse tumors were irradiated by a 625 nm LED (120 mW/cm$^2$, 5 min) at 24 h post-injection. The tumor volume and body weight were measured during the treatment period. As shown in FIGS. 10 and 11, the group treated with BC&Pt@PLA-PEG-cRGDfK+light irradiation exhibited significant tumor-growth inhibition compared with the group treated with PBS+light irradiation and free CAB. The group treated with BC&Pt@PLA-PEG-cRGDfK showed rapid tumor growth compared with the group of BC&Pt@PLA-PEG-cRGDfK+light irradiation. The obvious body weight loss in all groups was not observed, indicating unnoticeable systemic toxicity of the polymeric micelles and light irradiation. The treatment parameters will be optimized to enhance the antitumor efficacy, such as the injection frequency of the formulations, interval between injection and light irradiation, and CAB concentration.

The cytotoxicity of the BODIPY derivatives and PtTPBP is minimal,[10] which indicates good biocompatibility of these materials in biomedical applications. Our drug release strategy is the first example of developing the phototriggered drug delivery system through TTET process, where prodrug can be directly excited to the triplet excited state that allows photocleavage reactions to release free drugs. Moreover, the energy transfer process utilized here is much simpler than that of the cases reported before,[7] minimizing the unexpected energy consumption to improve the photocleavage efficiency. Furthermore, the photorelease wavelength was red-shifted to 625 nm. The red-light excitation is less toxic to cells and allows deeper tissue penetration than UV light, which could trigger more efficient drug release in biological tissues. The developed photocleavage strategy provides a new technique for designing highly efficient photoresponsive drug release systems for various diseases.

Those skilled in the art will recognize, or be able to ascertain many equivalents to the specific embodiments of the invention described herein using no more than routine experimentation. Such equivalents are intended to be encompassed by the following claims.

All publications, patents and patent applications mentioned in this specification are incorporated herein by reference in their entireties into the specification to the same extent as if each individual publication, patent or patent application was specifically and individually indicated to be incorporated by reference in its entirety.

Citation or discussion of a reference herein shall not be construed as an admission that such is prior art to the present invention.

REFERENCES

[1] (a) M. Karimi, A. Ghasemi, P. S. Zangabad, R. Rahighi, S. M. M. Basri, H. Mirshekari, M. Amiri, Z. S. Pishabad, A. Aslani, M. Bozorgomid, D. Ghosh, A. Beyzavi, A. Vaseghi, A. R. Aref, L. Haghani, S. Bahrami, M. R. Hamblin, Smart micro/nanoparticles in stimulus-responsive drug/gene delivery systems, *Chemical Society Reviews*, 2016, 45, 1457-1501; (b) Z. Liu, W. Wang, R. Xie, X. Ju, L. Chu, Stimuli-responsive smart gating membranes, *Chemical Society Reviews*, 2016, 45, 460-474; (c) Y. Shen, X. Fu, W. Fu, Z. Li, Biodegradable stimuli-responsive polypeptide materials prepared by ring opening polymerization, *Chemical Society Reviews*, 2015, 44, 612-622

[2] (a) M. Karimi, P. S. Zangabad, S. B. Ravari, M. Ghazadeh, H. Mirshekari, M. R. Hamblin, Smart nanostructures for cargo delivery: uncaging and activating by light, Journal of the American Chemical Society, 2017, 139, 4584-4610; (b) T. § olomek, J. Wirz, P. Klan, Searching for improved photoreleasing abilities of organic molecules, *Accounts of Chemical Research*, 2015, 48, 3064-3072.

[3] A. Y. Rwei, W. Wang, D. S. Kohane, Photoresponsive nanoparticles for drug delivery, *Nano Today*, 2015, 10, 451-467.

[4] (a) J. Zhou, Q. Liu, W. Feng, Y. Sun, F. Li, Upconversion luminescent materials: advances and applications, *Chemical Reviews*, 2015, 115, 395-465; (b) F. Wang, X. Liu, Recent advances in the chemistry of lanthanide-doped upconversion nanocrystals, *Chemical Society Reviews*, 2009, 38, 976-989; (c) J. Zhao, S. Ji, H. Guo, Triplet-triplet annihilation based upconversion: from triplet sensitizers and triplet acceptors to upconversion quantum yields, *RCS Advances*, 2011, 1, 937-950.

[5] J. Liu, W. Bu, L. Pan, J. Shi, NIR-triggered anticancer drug delivery by upconverting nanoparticles with integrated azobenzene-modified mesoporous silica, *Angewandte Chemie International Edition*, 2013, 52, 4375-4379.

[6] L. Zhao, J. Peng, Q. Huang, C. Li, M. Chen, Y. Sun, Q. Lin, L. Zhu, F. Li, Near-infrared photoregulated drug release in living tumor tissue via yolk-shell upconversion nanocages, *Advanced Functional Materials*, 2014, 24, 363-371.

[7] (a) W. Wang, Q. Liu, C. Zhan, A. Barhoumi, T. Yang, R. G. Wylie, P. A. Armstrong, D. S. Kohane, Efficient triplet-triplet annihilation-based upconversion for nanoparticle phototargeting, *Nano Letters*, 2015, 15, 6332-6338; (b) Q. Liu, W. Wang, C. Zhan, T. Yang, D. S. Kohane, Enhanced precision of nanoparticle phototargeting in vivo at a safe irradiance, *Nano Letters*, 2016, 16, 4516-4520; (c) D. S. Kohane, W. Wang, Q. Liu, Triplet-triplet annihilation-based upconversion, WO Application, WO2017004310A1, 2017-01-05.

[8] L. Huang, Y. Zhao, H. Zhang, K. Huang, J. Yang, Gang Han, Expanding anti-stokes shifting in triplet-triplet annihilation upconversion for in vivo anticancer-prodrug activation, *Angewandte Chemie International Edition*, 2017, 56, 14400-14404.

[9] (a) P. P. Goswami, A. Syed, C. L. Beck, T. R. Albright, K. M. Mahoney, R. Unash, E. A. Smith, A. H. Winter, BODIPY-derived photoremovable protecting groups unmasked with green light, *Journal of the American Chemical Society*, 2015, 137, 3783-3786; (b) T. Slanina, P. Shrestha, E. Palao, D. Kand, J. A. Peterson, A. S. Dutton, N. Rubinstein, R. Weinstain, A. H. Winter, P. Klan, In search of the perfect photocage: structure-reactivity relationships in meso-methyl BODIPY photoremovable protecting groups, *American Chemical Society*, 2017, 139, 15168-15175.

[10](a) L. Li, K. Li, M. Li, L. Shi, Y. Liu, H. Zhang, S. Pan, N. Wang, Q. Zhou, X. Yu, BODIPY-based two-photon fluorescent probe for real-time monitoring of lysosomal viscosity with fluorescence lifetime imaging microscopy, *Analytical Chemistry*, 2018, 90, 5873-5878; (b) A. H. A., S. Sreedharan, F. Ali, C. G. Smythe, J. A. Thomas, A. Das, Polysulfide-triggered fluorescent indicator suitable for super-resolution microscopy and application in imaging, *Chemical Communications*, 2018, 54, 3735-3738; (c) H. Zhu, J. Fan, J. Wang, H. Mu, X. Peng, An "enhanced PET"-based fluorescent probe with ultrasensitivity for imaging basal and elesclomol-iduced HCO in cancer cells, *Journal of the American Chemical Society*, 2014, 136, 12820-12823; (d) L. M. Tapia, R. S. Funosas, C. Zhao, F. Albericio, N. D. Read, R. Lavilla, M. Vendrell, Preparation of a Trp-BODIPY fluorogenic amino acid to label peptides for enhanced live-cell fluorescence imaging, *Nature Protocols*, 2017, 12, 1588-1619; (e) Q. Liu, B. Yin, T. Yang, Y. Yang, Z. Shen, P. Yao, F. Li, A general strategy for biocompatible, high-effective upconversion nanocapsules based on triplet-triplet annihilation, Journal of the American Chemical Society, 2013, 135, 5029-5037.

The invention claimed is:

1. A composition, comprising: a photosensitizer; a cleavable moiety that accepts triplet-triplet energy transfer from the photosensitizer in a higher energy state to cause cleavage of the cleavable moiety; and a releasable moiety releasable from the composition upon cleavage of the cleavable moiety, wherein the composition does not comprise an annihilator, wherein the photosensitizer is platinum II tetraphenyl tetrabenzoporphyrin (PtTPBP), the composition comprises a therapeutically-effective amount of a prodrug, the prodrug comprising the cleavable moiety and the releasable moiety, wherein the prodrug is BODIPY-CAB represented by the following structural formula

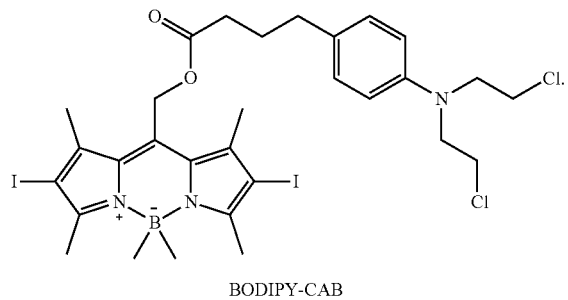 [SMILES: CC1=C(I)C(C)=[N+]2C1=C(COC(=O)CCCc1ccc(N(CCCl)CCCl)cc1)c1c(C)c(I)c(C)n1[B-]2(C)C]

BODIPY-CAB

2. The composition of claim 1 wherein the photosensitizer has an excitation wavelength of between 600 nm, and 1200 nm.

3. The composition of claim 2 wherein the photosensitizer has an excitation wavelength of between 600 nm and 700 nm.

4. The composition of claim 3 wherein the photosensitizer has an excitation wavelength of 625 nm.

5. The composition of claim 1 wherein the cleavable moiety is photocleavable.

6. The composition of claim 1 further comprising a carrier material.

7. The composition of claim 6 wherein the carrier material comprises the photosensitizer and the cleavable moiety.

8. The composition of claim 6 wherein the carrier material further comprises the releasable moiety.

9. The composition of claim 6 wherein the carrier material comprises a polymer.

10. The composition of claim 9 wherein the carrier material comprises a particle.

11. The composition of claim 10 wherein the particle has an average diameter of less than 1 mm.

12. The composition of claim 6 wherein the carrier material comprises a film.

13. The composition of claim 6 wherein the carrier material comprises a polymeric micelle.

14. A method comprising applying to a subject, a composition comprising a photosensitizer to transfer triplet-triplet energy from the photosensitizer to a cleavable moiety to cause cleavage of the cleavable moiety and release of a releasable moiety from the composition; and applying light to the subject to cause the cleavage of the cleavable moiety, wherein the triplet-triplet energy is not transferred via an annihilator,
   wherein
     the photosensitizer is platinum II tetraphenyl tetrabenzoporphyrin (PtTPBP),
     the composition comprises a therapeutically-effective amount of a prodrug, the prodrug comprising the cleavable moiety and the releasable moiety, wherein the prodrug is BODIPY-CAB represented by the following structural formula

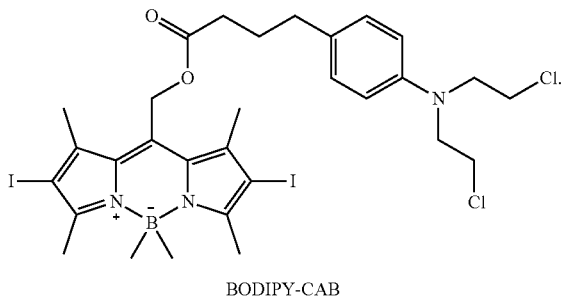 [SMILES: CC1=C(I)C(C)=[N+]2C1=C(COC(=O)CCCc1ccc(N(CCCl)CCCl)cc1)c1c(C)c(I)c(C)n1[B-]2(C)C]

BODIPY-CAB

15. The method of claim 14 wherein the light is coherent.

16. The method of claim 14 wherein the light is noncoherent.

* * * * *